United States Patent [19]

Sterzer

[11] 4,282,887
[45] Aug. 11, 1981

[54] RIDGE-WAVEGUIDE APPLICATOR FOR TREATMENT WITH ELECTROMAGNETIC ENERGY

[75] Inventor: Fred Sterzer, Princeton, N.J.

[73] Assignee: RCA Corporation, New York, N.Y.

[21] Appl. No.: 83,638

[22] Filed: Oct. 11, 1979

[51] Int. Cl.³ .............................................. A61N 1/40
[52] U.S. Cl. .............................. 128/804; 219/10.55 R
[58] Field of Search ...................... 123/783, 804, 422; 219/10.55 R, 10.55 A

[56] References Cited

U.S. PATENT DOCUMENTS

| | | | |
|---|---|---|---|
| 2,814,298 | 11/1957 | Argento | 128/804 X |
| 3,065,752 | 11/1962 | Potzl | 128/422 |
| 3,077,195 | 2/1963 | Folsche | 128/804 |
| 3,456,355 | 7/1969 | Cumming et al. | 219/10.55 A X |
| 4,108,147 | 8/1978 | Kantor | 128/804 |
| 4,119,102 | 10/1978 | LeVeen | 128/804 |
| 4,140,130 | 2/1979 | Storm | 128/804 |

FOREIGN PATENT DOCUMENTS

| | | | |
|---|---|---|---|
| 2417263 | 10/1975 | Fed. Rep. of Germany | 128/804 |
| 862646 | 3/1961 | United Kingdom | 128/804 |

OTHER PUBLICATIONS

Lehmann et al., "Evaluation . . . Contact Applicator", Arch. Phys. Med. and Rehab., Mar. 1970, pp. 143–146.

Primary Examiner—Lee S. Cohen
Attorney, Agent, or Firm—Samuel Cohen; Robert L. Troike

[57] ABSTRACT

An applicator for the therapeutic treatment of a patient with electromagnetic energy is provided by a ridge waveguide filled with deionized water and having a sheet of flexible radio frequency transparent material covering the radiating open end. The waveguide with the ridge and filled with water is dimensioned to propagate radio frequency signals in the $TE_{10}$ mode.

7 Claims, 7 Drawing Figures

RIDGE-WAVEGUIDE APPLICATOR FOR TREATMENT WITH ELECTROMAGNETIC ENERGY

This invention relates to the therapeutic treatment of living tissue with electromagnetic energy and more particularly, to the treatment of tissue using radio frequency signals which are of relatively long wavelengths.

Medical practioners know that a patient with a cancerous tumor can be treated by a process which raises and maintains the temperature of a tumor to a typical value of 43° C. One method for raising the temperature of the treated tissue is by the use of electromagnetic signals. The temperature of the tissue irradiated by the electromagnetic signals is a function of the power or intensity of the electromagnetic signals provided to the body tissue. The depth of the penetration of the electromagnetic signals into the tissue is generally a direct function of the type of tissue and an inverse function of the frequency of the signal applied. The dimensions and the shape of the irradiated volume of tissue are dependent on parameters such as the type of tissue, the frequency of the electromagnetic signals and the radiation pattern of the electromagnetic signals.

The tissue heated by the electromagnetic signals has transitional or boundary conditions caused by changes in its dielectric constant. For example, an irradiating signal applied to the body may encounter skin, then fat and then muscle tissue having different dielectric constants. The electric field of the irradiating signals can have components normal to and parallel to skin, fat and muscle tissue.

A radiation pattern having the primarily normal component can be achieved by using two applicators, each having the form of a paddle, and each connected to an electromagnetic signal source. In use the paddles are positioned opposite each other on opposite surfaces of the body with the body tissue sandwiched between the paddles. See for example, U.S. Pat. No. 4,140,130 of Storm, III, or U.S. Pat. No. 4,119,102 of LeVeen. However, in such an arrangement a portion of the sandwiched tissue, such as the heart organ, may be adversely affected by the irradiating electromagnetic signals. In addition, the normal component of the electric field can produce excessive heating in the fat tissue.

For deep heating into muscles or deep seated tumors it is preferable to have radiation fields with the electric field primarily parallel to the surface of the body and to the fat-muscle interface, i.e. an electric field perpendicular to the direction of energy flow. Therefore, there remains a need in the diathermy and hyperthermia art for a single-ended applicator that applies electromagnetic signals to the body with the electric field primarily parallel to the surface of the body and body layers.

In accordance with an embodiment of the present invention, a direct contact applicator is provided for localized therapeutic treatment of living tissue of a patient with electromagnetic wave signals. The applicator includes a ridge waveguide having one end covered with a substantially radio frequency transparent material adapted to conform to the patient in the region adjacent the ridge. The waveguide is filled with a low-loss, high-dielectric medium. The waveguide is dimensioned to propagate the electromagnetic signals applied thereto as transverse electric mode waves, whereby the electric field is applied parallel to the surface of the patient, and to concentrate the electromagnetic signal energy in the region of the ridge and thereby provide localized heating of the tissue.

As discussed in connection with the prior art, the depth of the penetration of rf (radio frequency) electromagnetic signals to treat a tissue is generally a direct function of the type of tissue and an inverse function of the frequency of the signal. The lower the frequency, the greater the depth of penetration. The lower rf frequencies, for example, 27 MHz, are important for treating, for example, deep seated tumors. As the irradiating signal penetrates the treated tissue it encounters different types of tissue. For example, the irradiating signal externally applied to the body for heating deep seated tumors first encounters the skin, then a fat layer of tissue and then a muscle layer of tissue. The electric field pattern of the irradiating signals may have components normal to and parallel to the surface of these layers. The normal component of the electric field intercepts, penetrates, and excessively heats the fat layer relative to the muscle layer. In particular, excessive heating is caused at the fat-muscle interface.

The parallel component of the electric field intercepts and penetrates and heats the desired muscle layer greater than the fat layer. Therefore, it is preferable to provide rf signal irradiating fields with the electric field component primarily parallel to the surface of the fat-muscle interface. Such a signal is provided when the signal is launched from a waveguide supporting the dominant transverse electric ($TE_{10}$) mode field distribution. A rectangular waveguide conventionally used for hyperthermia patients would have dimensions that are quite large to support this mode for a signal frequency on the order of 27 MHz. For example, the required longest aperature dimension (x-dimension in FIG. 1), of the rectangular waveguide, for a 27 MHz signal is 5.55 meters. Accordingly, a rectangular waveguide of an x dimension of 5.55 meters would be costly and also the area of the treatment would be quite large. Also such a large waveguide would require an excessive amount of power to achieve the desired heating.

Figure 1:
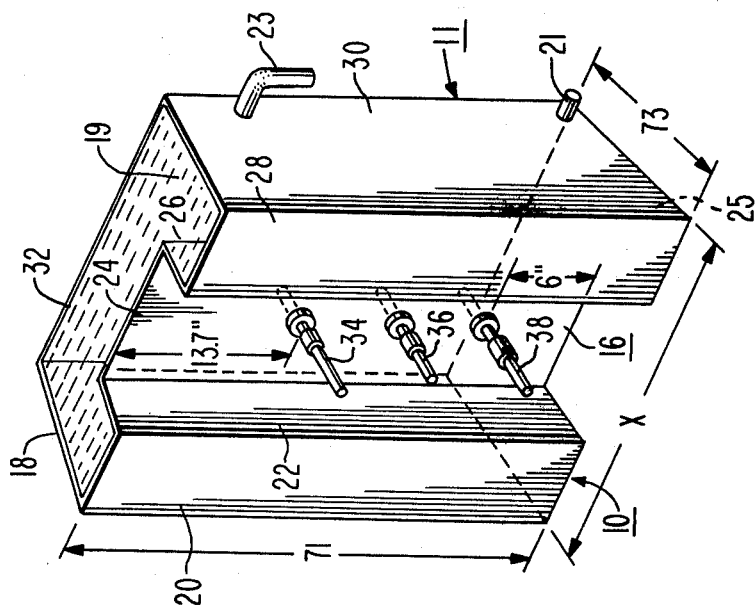
FIG. 1 is a front perspective view of an applicator in accordance with one embodiment of the present invention.

In accordance with the present invention, an applicator is provided which both reduces the required aperture dimension to support this desirable transverse electric $TE_{10}$ mode and the area of treatment when using signal frequencies on the order of the 27 MHz. Referring to FIG. 1, the applicator 10 embodying the present invention includes a ridge waveguide 11 filled with deionized water. The ridge waveguide reduces the size dimension in the x-direction (longest aperture dimension) and at the same time concentrates the field in the region of the ridge to reduce the area of treatment. The deionized water further reduces all dimensions including the required size of the aperture dimension of the ridge waveguide with a non-rf absorbing material while at the same time providing an impedance which more closely matches that of the body to be treated.

Referring to FIG. 1, there is illustrated a perspective view of the applicator 10 for applying electromagnetic signals to the body. Applicator 10 includes asymmetrical ridge waveguide 11 formed as shown in FIG. 1 by conductive walls 18, 20, 22, 24, 26, 28, 30 and 32. The walls 22, 24 and 26 form a ridge 16. The waveguide 11 is closed at one longitudinal end 25, hereinafter termed the shorted end by a conductive wall and electrically open at the other end for launching the electromagnetic signals. For an applicator designed for 27 MHz, by way of example; all the walls 18, 20, 22, 24, 26, 28, 30 and 32 have a typical height of 76.2 centimeters (cm) (30 inches), shown as distance 71, and a typical thickness of 0.0635 centimeters (0.025 inch). Side walls 18 and 30 for the example have a width of 26.29 centimeters (10.35 inches), shown as distance 73. Front walls 20 and 28 for the example are 14.60 centimeters (5.75 inches) wide. Ridge 16 walls 22, 24 and 26 for the example are 12.57 cm (4.95 inches), 11.5 inches (29.2 cm) and 4.95 inches (12.57 cm), respectively. Back wall 32 for the example has a width of 58.42 centimeters (23 inches in x-direction) and longitudinal length of 76.2 centimeters (30 inches) shown as distance 71. Metal tuning rods 34, 36 and 38 extend through the wall 24. Tuning rods 34, 36 and 38 are utilized to adjust the impedance of the ridge waveguide 11 with respect to the impedance of the treated tissue. The tuning rods 34, 36 and 38 may be adjustable plunger-type rods which extend adjustable distances through wall 24 into the waveguide. Rod 38 for the example is about 15.2 cm (6 inches) from shorted end 25 and rod 34 is 34.8 cm (13.7 inches) from open end. Rod 36 is centered between rods 34 and 38. Electromagnetic signals from a source (to be described in more detail later) are applied to the waveguide via a radiator-coupler 35 (see FIG. 2). The radiator-coupler 35 for the example extends through the wall 32 about 30.7 cm (12.1 inches) from shorted end 25. The radiator-coupler may be, for the example, a coaxial probe with the center conductor of the coaxial cable extending 12.7 centimeters (5 inches) in insulative manner through wall 32 into the ridge waveguide 11 and the outer conductor is directly connected to the wall 32. The radiator-coupler 35 is positioned a quarter wavelength at the electromagnetic signal frequency from shorted end wall 25.

The ridge waveguide 11 is filled with a non-rf absorbing dielectric material such as deionized water 19. The water with its dielectric constant of about 80 reduces the dimensions of the waveguide required for the electromagnetic signal and provides an impedance like that of living tissue of the body. Further, the deionization of the water reduces the power dissipation of a signal within the ridge waveguide due to its non-rf absorbing characteristics. Ridge waveguide 11 is provided with suitable valves 21 and 23 for connection to a negative pressure source (not shown) and a source of deionized water (not shown) respectively.

Figure 2:
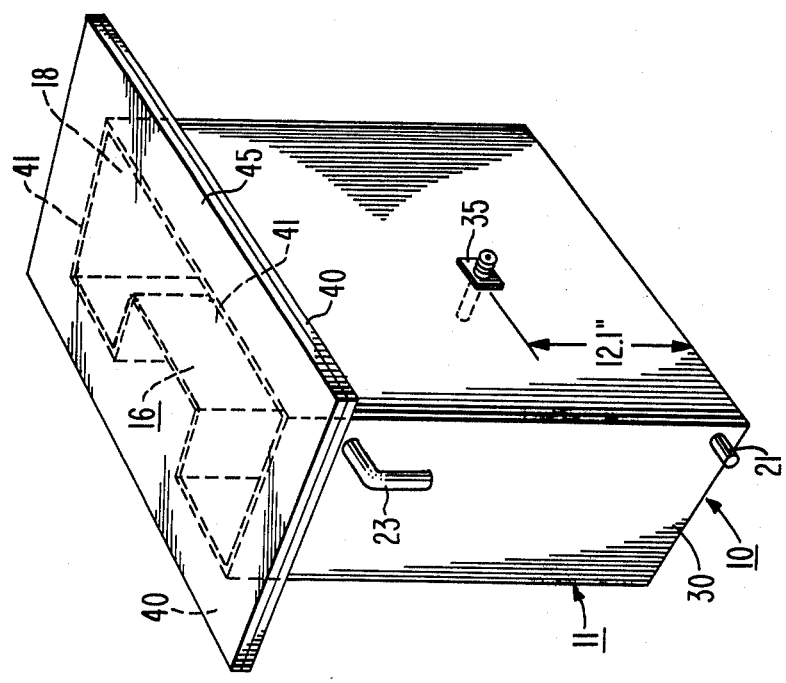
FIG. 2 is a rear perspective view of the applicator of FIG. 1 with an elastic end cover.

Reference is now made to FIG. 2 illustrating the applicator 10 with a suitably attached metal sheet 40. Metal sheet 40 has a cut out 41 that matches the entire opening of waveguide 11. The metal sheet 40 and the cut out 41 of the applicator 40 are covered by a thin sheet 45 of a flexible waterproof nonconductive material such as rubber. The sheet of rubber material and the water allow the shape of the applicator to conform with the shape of the body placed over the open or radiating end of the waveguide.

In the operation of the applicator 10 as shown in FIGS. 1 and 2 the radiator-coupler 35 excites electromagnetic signal waves in the $TE_{10}$ mode in the waveguide 11. The radiator-coupler 35 is positioned one quarter wavelength from the shorted end 25 of the ridge waveguide 11 of FIGS. 1 and 2. The wave launched from the radiator-coupler 35 which is at the end 25 of the waveguide and is reflected back in phase to combine with the wave launched towards the open end. The signal is coupled along the waveguide and is radiated out of the ridge waveguide through the rubber sheet 45 at opening 41. The maximum field intensity as indicated in FIG. 3 is substantially concentrated about the ridge 16 and particularly between the ridge 16 and opposite wall 32.

Figure 3:
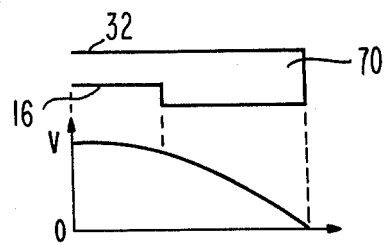
FIG. 3 illustrates the approximate voltage distribution across half of the cross section of a ridge waveguide.

Reference is now made to FIG. 3 to discuss the radiation field of wave in applicator 10. The structure of a ridge type waveguide provides for a voltage distribution shown in FIG. 3. The voltage is maximum and fairly constant in the region between the ridge 16 and the rear wall 32. This provides nearly uniform heating. The voltage level drops dramatically in the region 70 beyond the ridge.

Figure 4:
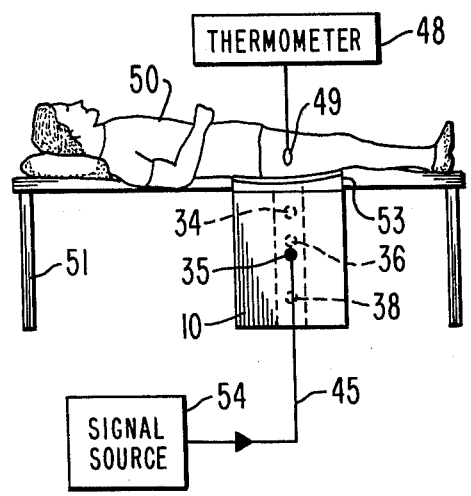
FIG. 4 is a system block diagram of an apparatus for treatment of the body using the applicator of the present invention.

Referring to FIG. 4 there is illustrated a system using the applicator 10. The patient 50 is positioned on a bed 51. A portion 53 of the bed 51 is cut away and the applicator 10 is inserted in the cutaway portion. The patient 50 is positioned with the area to be treated over the sheet 45 of rubber material of the applicator 10. For the example of the treatment of a patient's thigh, the thigh is placed over the applicator 10 and on the sheet 45 with the treatment area directly above the high field region between the ridge 16 and the opposite wall. Signals from a source 54 (for the example 27 MHz signals) are applied to the applicator 10 via a coaxial cable 45 connected to radiator-coupler 35. A thermocouple 49 may periodically be placed on the thigh to sense the thigh temperature. A thermometer 48 coupled to the thermocouple provides a signal indicative of the temperature at the thigh. The signals from the source 54 are interrupted when the thermocouple is placed on the patient to make measurements and to prevent overheating. The tuning rods 34, 36 and 38 are adjusted to reduce the reflected power as indicated on a suitable power meter (not shown) attached to source 54.

In a hyperthermia treatment of cancer such as malignant tumors in the leg, the cancerous tumor is preferably heated to a hyperthermia temperature of about 43° C. (the temperature typically is maintained in the aproximately 42°-43.5° C. temperature range) for a period of one-half to one hour. Further, it is desirable that during the treatment of cancerous lesions, the healthy tissue be kept at a temperature close to the body temperature of 37° C. It should be understood that the practice of the invention is not limited to the treatment of a leg and that it can be used in the treatment of any surface tissue skin, etc. or internal body tissue that is positioned over the ridge of the applicator 10. By terminating the end of the waveguide in a sheet or rubber flexible rubber material and filling the waveguide with water, the end of the guide conforms to the body to provide a better coupling and to aid in the comfort of the patient being treated. The applicator 10 may be arranged with a suitable fixture to provide a chair structure to allow the patient to be seated over the ridge 16 of applicator 10. In such arrangement, the patient may receive therapeutic treatment of a rectal-type cancerous lesion.

Figure 5:
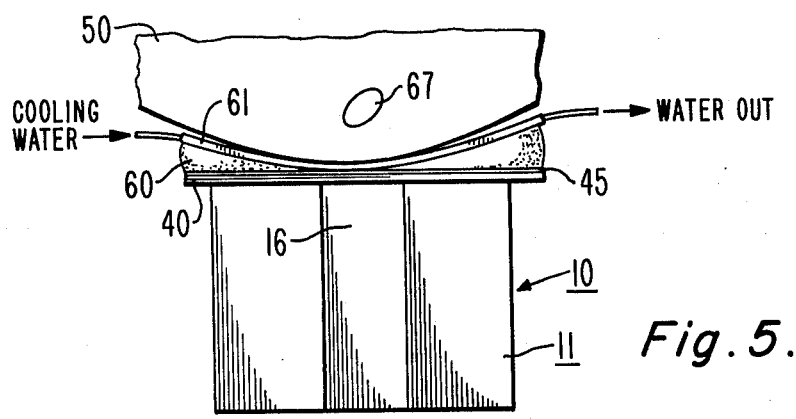
FIG. 5 is an elevation view of the applicator of FIG. 4 with an additional lossy material pad and a cooling pad.
Figure 6:
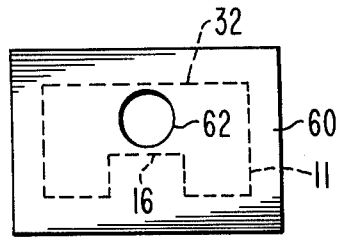
FIG. 6 is a top view of the applicator in FIG. 5 with the cooling pad removed.
Figure 7:
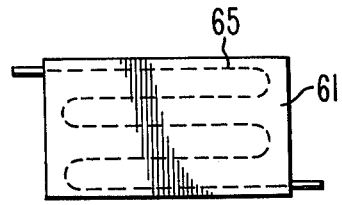
FIG. 7 illustrates the cooling pad.

Referring to FIG. 5, there is illustrated the applicator 10 having a flexible pad 60 of rf (radio frequency) lossy material and a cooling pad 61 on top of the sheet 45 of flexible rubber material which covers the opening of the waveguide 11. The flexible rf lossy material pad 60 extends over the top of the sheet 45 of rubber and has an opening 62 centered with respect to the aperture of the waveguide and over the high field region between the ridge 16 and the opposite wall. (See FIG. 6.) The cooling pad 61 is a pad of flexible waterproof material having a network 65 of plastic or rubber tubes therein that pass cooling water (see FIG. 7). Fresh cooling water is passed through the network 65. The cooling pad 61 extends above and over the flexible pad 60 of rf lossy material. The rf lossy material may be paper padding material soaked in a saline water solution. The paper pads in a water solution act as an impedance like that of a patient and the salt provides the rf loss. The patient is positioned on the cooling pad and the area 67 of the patient 50 to be heated is positioned above the opening 62. The rf absorbing pad 60 causes rf loss in the region beyond the opening 62 to protect the patient and limit the area of treatment. The cooling pad 61 allows the power level to be increased without damage to the surface tissue of the patient.

What is claimed is:

1. A direct contact applicator for localized electromagnetic energy treatment of living tissue of a patient with signals at a desired radio frequency where for the desired treatment depth the wavelength is relatively long compared to a desired area of treatment comprising:

a waveguide having a ridge extending along the longitudinal length thereof, said waveguide being filled with a low loss and high dielectric medium like that of said patient, said waveguide including said ridge being dimensioned to propagate said signals therein as transverse electric mode waves where there is relatively little electric field component in the direction of propagation of said waves and to concentrate the signal energy in the region adjacent the ridge;

a substantially radio frequency transparent material adapted to conform to a body surface of said patient covering one end of said ridge waveguide; and means coupled to said waveguide for applying said signals thereto for exciting propagation thereof in said transverse electric mode, whereby said signals are applied to said patient with the electric field component primarily parallel to said body surface.

2. The combination of claim 1 wherein said medium is deionized water.

3. The combination of claim 2 wherein said radio frequency transparent material is flexible waterproof material.

4. The combination of claim 3 wherein said material is of rubber.

5. The combination of claim 1 wherein said desired radio frequency is about 27 MHz.

6. The combination of claim 1 including a pad of rf lossy material extending over said radio frequency transparent material and having an aperture in the region adjacent the ridge to limit the area of treatment.

7. The combination of claim 6 including a cooling pad adjacent said pad of rf lossy material for cooling said pad of rf lossy material.

* * * * *